United States Patent [19]

Treves et al.

[11] Patent Number: 4,467,095
[45] Date of Patent: Aug. 21, 1984

[54] ANTICHOLINERGIC COMPOUNDS

[75] Inventors: Gino R. Treves; Burton M. Baum, both of Princeton, N.J.

[73] Assignee: FMC Corporation, Philadelphia, Pa.

[21] Appl. No.: 800,350

[22] Filed: Feb. 10, 1969

[51] Int. Cl.³ .......................................... C07D 211/70
[52] U.S. Cl. ................................................ 546/342
[58] Field of Search ............ 260/295 R, 295 S, 297 R; 546/342

[56] References Cited

U.S. PATENT DOCUMENTS

| | | | |
|---|---|---|---|
| 3,399,206 | 8/1968 | Kühnis et al. | 260/297 |
| 3,627,775 | 12/1971 | Hubner et al. | 546/342 |
| 3,786,059 | 1/1974 | Walker et al. | 546/342 |
| 3,879,556 | 4/1975 | Walker et al. | 424/263 |

OTHER PUBLICATIONS

Burger, "Drugs Affecting the Central Nervous System", vol. 2, pp. 128-132 and 139, Marcel Dekker, Inc., (Mar. 1968), N.Y.
Mutschler, Arzneimittel-Forsch., 16(1), 73-5, (1966), [and abstract thereof; C.A., 65, 1224e, (1966)].
Morrison and Boyd, Organic Chemistry, p. 626, Allyn & Bacon, Inc., (1959), Boston.

Primary Examiner—Edward A. Miller
Attorney, Agent, or Firm—R. D. Jackson; M. Zucker; E. G. Seems

[57] ABSTRACT

Glycolic esters, useful as anticholinergic drugs, have the formula

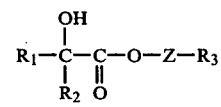

wherein $R_1$ is selected from the class consisting of phenyl and cyclopentyl; $R_2$ represents a hydrocarbon radical of 3 to 6 carbon atoms; Z is selected from the class consisting of $-CH_2-$, $-CH_2CH_2-$ and $-CH_2CH=$ and $R_3$ represents an azacyclic ring selected from the class consisting of 1-methyltetrahydropyridine, 1-methyl-3-pyrroline, quinuclidine, 2-tropidine and 1-azabicyclo[2.2.2]oct-2-ene.

2 Claims, No Drawings

ANTICHOLINERGIC COMPOUNDS

BACKGROUND OF THE INVENTION

A. Field of the Invention

This invention relates to compounds useful as anticholinergic drugs and in particular to those belonging to the class of dihydrocarbon substituted glycolic esters in which the esterifying alcohol is a tertiary nitrogen-containing, cyclic compound.

B. Description of the Prior Art

It is known that esters of a basic nitrogen-containing alcohol and a substituted glycolic acid such as benzylic acid or α-cyclopentyl-α-phenylglycolic acid have marked anticholinergic activity, and various members of this class have been reported to exhibit useful cycloplegic or mydriadic action and to be of value in treating mental illnesses, certain neurological diseases and disorders of the gastrointestinal tract. However, the known drugs used in the treatment of these maladies often prove unsuitable due to unsatisfactory time-action courses. They tend to react only after a considerable onset period, and the effects generally persist too long. Manifestly, there is a need for anticholinergic drugs which will function shortly after administration, and the need is especially acute for drugs whose effects wear off rapidly, such as in the cycloplegic diagnostic examination of the eyes.

SUMMARY OF THE INVENTION

It has now been discovered that the desiderata aforesaid are possessed to a substantial degree by a new family of disubstituted glycolic esters of the formula

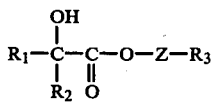

wherein $R_1$ is selected from the class consisting of phenyl and cyclopentyl; $R_2$ represents a hydrocarbon radical of 3 to 6 carbon atoms; Z is selected from the class consisting of —$CH_2$—, —$CH_2CH_2$— and —$CH_2CH$=; and $R_3$ represents an azacyclic ring selected from the class consisting of 1-methyltetrahydropyridine, 1-methyl-3-pyrroline, quinuclidine, 2-tropidine and 1-azabicyclo[2.2.2]oct-2-ene, and the provision of such compounds and their use as anticholinergic drugs constitutes the principal object and purpose of the present invention. Other objects and purposes will become manifest subsequently.

DESCRIPTION OF THE INVENTION AND THE PREFERRED EMBODIMENTS

As can be seen from an inspection of the structural formula aforesaid, the anticholinergic compounds herein are dihydrocarbon substituted glycolates, in which the esterifying moiety is an azacyclic alcohol of the type in which the alcohol function is attached to a heterocyclic ring through a lower alkylene bridge system. Generally speaking, they can be prepared by the known methods of ester syntheses. An especially convenient procedure consists of reacting the requisite disubstituted glycolic acid with the appropriate azacyclic alcohol in the presence of dimethylformamide (DMF) dineopentyl acetal according to the method of Buchi et al of preparing benzyl carboxylates, and described in Agnew. Chemie, 75, 1176 (1963). The reaction can be visualized by a reference to the following equation:

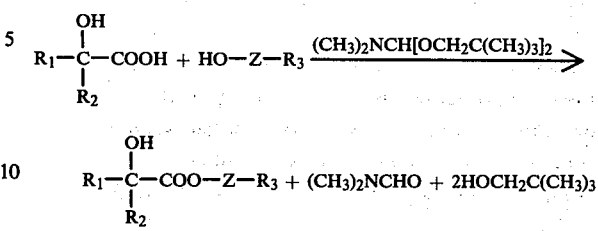

wherein $R_1$, $R_2$, $R_3$ and Z have the significance aforesaid.

Another ester synthesis suitable for realizing the compounds of the invention is the transesterification of the appropriately disubstituted glycolate ester wherein the esterifying alcohol is a lower alcohol with the requisite azacyclic alcohol in the presence of a basic catalyst according to the following scheme:

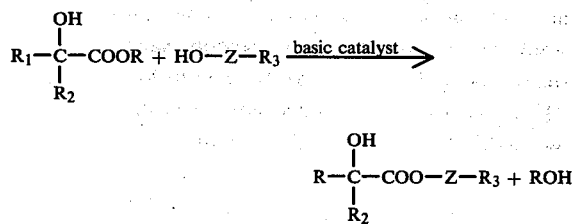

wherein R is a lower alkyl group, e.g. methyl, ethyl, etc. The transesterification is carried out in the presence of a relatively inert, normally liquid organic solvent such as an aromatic or saturated aliphatic hydrocarbon; suitable examples are benzene, toluene, hexane, heptane and the like. Basic catalysts are commonly the alkali metals or their alkoxides; sodium or sodium ethoxide are most often employed. An especially convenient procedure is to reflux the components in such a manner whereby the lower alcohol, i.e. ROH, formed during the reaction, can be distilled from the reaction vessel; a suitable apparatus is the well-known Dean-Stark separator.

The ester product is conveniently isolated in the form of its acid addition salt, which is purified by crystallization from an organic solvent in the usual manner.

The dihydrocarbon substituted glycolic acids and the lower alkyl esters thereof, are known entities, the description and preparation of which is detailed in the chemical literature. Any particular member, not specifically disclosed in the prior art, can be prepared by application of the known methods.

The azacyclic alcohols are likewise a known chemical class, although certain specific members described in detail elsewhere herein have not been suggested previously. Generally, both the known and new members can be prepared, utilizing syntheses familiar in the art.

The compounds of the present invention are conveniently administered in the form of isotonic solutions of their acid addition salts. These are readily produced by contacting the free ester base with a suitable acid in the presence of a solvent such as acetone, benzene, ethanol, isopropanol, ether, or the like. Exemplary acids suitable for the purpose aforesaid are hydrochloric acid, sulfuric acid, citric acid, tartaric acid, succinic acid, benzoic acid, phosphoric acid, maleic acid, etc.

Quaternary ammonium salts are likewise a suitable form in which to administer the compounds of the invention, particularly for gastrointestinal disorders. These particular entities are realized by contacting the ester base with an appropriate alkalating agent such as a lower alkyl halide, as exemplified by methyl bromide, or ethyl chloride, a lower alkyl sulfate such as ethyl sulfate, or a phenylalkyl halide, or sulfate such as phenethyl chloride, benzyl sulfate or benzyl bromide.

The active agents of the invention can be administered to animals and humans as pure compounds. Normally however, it is advisable to first combine one or more of the compounds with a suitable pharmaceutical carrier to obtain a more satisfactory size to dosage relationship. Pharmaceutical carriers which are liquid or solid can be used. Preferably, the carrier is liquid, and in this connection it is conveniently an isotonic solution of the acid addition salt of the compounds herein. Flavoring materials can be included in these solutions as desired. Solid pharmaceutical carriers such as starch, sugar, talc and the like may be used to form powders. These can be directly administered to a patient or added to suitable foods and liquids, including water, to facilitate administration. The powders can also be compressed into tablets or contained in gelatin capsules. Suitable lubricants such as magnesium stearate, binders such as gelatin and disintegrating agents such as sodium carbonate in combination with citric acid are commonly used in forming the tablets.

Unit dosage forms such as tablets and capsules can contain any suitable pre-determined quantity of one or more of the active agents herein as a toxic salt and may be administered one or more at a time at regular intervals. Such unit dosage forms, however, should generally contain a concentration of 1.0% to about 50.0% by weight of one or more of the active compounds of the invention. Generally speaking, unit dosage forms range from about 5 to about 300 milligrams of active agents.

Reference is now made to the following examples:

PREPARATION OF DISUBSTITUTED GLYCOLIC ESTERS USING α-1-METHYLTETRAHYDROPYRIDINEALK-ANOL AS THE AZACYCLIC ALCOHOL

EXAMPLE 1

4-(1-Methyl-1,2,3,6-tetrahydropyridine)methyl-α-Isopropyl-α-phenylglycolate Hydrochloride

Method A

A solution of 3.88 g. (0.02 mole) of α-isopropyl-α-phenylglycolic acid, 1.4 g. (0.011 mole) of 4-(1-methyl-1,2,3,6-tetrahydropyridine)methanol and 3.0 g. (0.013 mole) of N,N-dimethylformamide dineopentyl acetal in 30 ml. of methylene chloride was allowed to stand overnight in a nitrogen atmosphere. The solvent was eliminated under reduced pressure; the residue was dissolved in ether and extracted with dilute hydrochloric acid. The acid extract was made basic with saturated potassium carbonate and then extracted with chloroform. The chloroform solution was dried over sodium carbonate and filtered. The solvent was eliminated under reduced pressure and the residue was washed with cold water. The chloroform solution of the insoluble oil was dried over sodium carbonate, filtered and the solvent removed. Hexane was added to the residue and a small amount of insoluble material was filtered off. Since no crystalline material was obtained, the hexane was eliminated and the residue dissolved in ether and converted to the hydrochloride salt by bubbling in dry hydrogen chloride. The solid obtained was filtered and dried, yielding 0.87 g. (23.6%) of product, m.p. 161°-2° C. This was recrystallized from ethyl acetate-ethanol to give 0.35 g. (m.p. 161°-2° C.) of purified material.

Method B

A 5-liter, three-neck flask was equipped with a stirrer, a thermometer, and a 24×0.5 inch vacuum jacketed, silverized column connected to a variable distilling head with electromagnetic coil and rectifier. The flask was charged with 115 g. (0.9 mole) of 4-(1-methyl-1,2,3,6-tetrahydropyridine)methanol (containing some 4-(1-methylpiperidine)methanol as an impurity), 187.2 g. (0.9 mole) methyl α-isopropyl-α-phenylglycolate and 2760 ml. of dry benzene. The mixture was heated under reflux while small pieces of sodium were added and the temperature at the still head reached 58° C. (benzene-methanol azeotrope). Reflux and variable take-off periods were alternated while small pieces of sodium were added. This was continued for several hours until the amounts of methanol in the distillate approached the expected theoretical amount as shown by NMR analysis. The cold mixture was filtered to eliminate any sodium which was still present and treated with four 500 ml. portions of N-hydrochloric acid. The combined hydrochloric acid solutions were covered with one liter of hexane and treated between 5°-8° C. with 200 ml. of cold 50% sodium hydroxide solution. The alkaline solution was extracted with another liter of hexane. Benzene was added to facilitate the separation of the last small amount of aqueous basic layer. The combined benzene-hexane solution was dried over sodium carbonate, filtered, and the solvent eliminated in vacuo. The residue was dissolved in five liters of ether, cooled with ice, and a stream of hydrogen chloride was passed through the solution until no more precipitate formed. The gummy product was washed with ether and crystallized from three liters of isopropanol. There was obtained 175 g. (57%) of material m.p. 162°-4° C.d.

Using the procedures of Example 1, the following disubstituted glycolic acids esterified with a 1-methyltetrahydropyridine were prepared.

TABLE I $$R_1-\underset{\underset{R_2}{|}}{\overset{\overset{OH}{|}}{C}}-COO-Z-R_3$$

| Example | Method | R₁ | R₂ | R₃ | Z | B.P. °C. (mm) M.P. °C. | MED₅₀ | LD₅₀ |
|---|---|---|---|---|---|---|---|---|
| 2 | A | C₆H₅ | C₆H₅ | 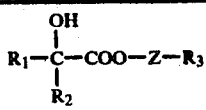 | —CH₂— | 115-30 | 0.002 | 18 |
| 3 | B | C₆H₅ | △ | " | " | 140-3 | 0.02 | 56 |
| 4 | B | C₆H₅ | ☐ | " | " | 194-6 | 0.003 | 56 |
| 5 | A | C₆H₅ | ⬠ | " | " | 141.5-142.5 | 0.008 | 42 |
| 6 | B | C₆H₅ | CH₃—C≡CH₂ | " | " | 117.5-119 | 0.02 | 24 |
| 7 | B | C₆H₅ | ⬠ | " | " | 108-110 | 0.008 | 11 |
| 8 | B | ⬠ | CH₃—C≡C— | " | " | 143-5(0.001) | 0.4 | 56 |
| 9 | B | C₆H₅ | CH≡C-C≡C—<br>CH₃ | " | " | 84.5-85.5 | 0.02 | 32 |
| 10 | B | C₆H₅ | C₆H₅ | " | —CH₂CH₂— | 92.3 | 0.02 | 18 |
| 11 | B | C₆H₅ | △ | " | " | 160(0.07) | 0.02 | 40 |
| 12 | B | C₆H₅ | ⬠ | " | " | 129-31 | 0.02 | 36 |
| 13 | B | C₆H₅ | —CH(CH₂)₂ | " | " | 140-50(0.01) | 0.06 | 50 |
| 14 | B | C₆H₅ | C₆H₅ | (N-methyl tetrahydropyridine with methyl) | —CH₂— | 98-100 | 0.02 | 18 |
| 15 | B | C₆H₅ | ⬠ | " | " | 199 | 0.002 | 56 |
| 16 | B | C₆H₅ | —CH(CH₃)₂ | " | " | 193-4 | 0.006 | 56 |
| 17 | B | C₆H₅ | CH₃—C′=CH₂ | " | " | 166-70 | 0.06 | 56 |

TABLE I-continued $$R_1-\underset{\underset{R_2}{|}}{\overset{\overset{OH}{|}}{C}}-COO-Z-R_3$$

| Example | Method | $R_1$ | $R_2$ | $R_3$ | Z | B.P. °C. (mm) M.P. °C. | Mouse Screen MED$_{50}$ | LD$_{50}$ |
|---|---|---|---|---|---|---|---|---|
| 18 | B | cyclopentyl | $CH_3-C\equiv C-$ | " | " | 145–6(.006) | 0.6 | 56 |
| 19 | B | $C_6H_5$ | cyclopentenyl | " | " | 108–109.5 | 0.06 | 50 |
| 20 | B | $C_6H_5$ | $CH_2=\underset{\underset{CH_3}{\mid}}{C}-C\equiv C-$ | " | " | 113–4 | 0.02 | 36 |
| 21 | B | $C_6H_5-$ | $C_6H_5-$ | 1,4-dimethyl-1,2,5,6-tetrahydropyridin-3-yl | $-CH_2-$ | 172–4 | 0.06 | 14 |
| 22 | B | $C_6H_5$ | cyclopentyl | " | " | 86–7 | 0.02 | 36 |
| 23 | B | $C_6H_5$ | cyclobutyl | " | " | 175–6 | 0.02 | 50 |
| 24 | B | $C_6H_5$ | $(CH_3)_2CH-$ | " | " | 155–6 | 0.02 | 63 |

The azacyclic alcohols, used in the aforedescribed Examples, were prepared as follows:

4-(1-methyl-1,2,3,6-tetrahydropyridine)methanol (Intermediate for Example 1)

To a solution of 12.0 g. (0.3 mole) of sodium borohydride in 100 ml. of absolute ethanol, 25.1 g. (0.1 mole) of 4-pyridinemethanol methiodide in 130 ml. of ethanol was added dropwise maintaining a temperature of between 15°–25° C. After remaining at room temperature for several hours, most of the ethanol was removed in vacuo. The products of two such runs were combined and treated with 200 ml. of water and extracted five times with 200 ml. portions of chloroform. The chloroform solution was dried over sodium sulfate, filtered, and the residue distilled to give 24.9 g. b.p. 78°–82° C. (0.7 mm). The aqueous residue was made strongly basic with a saturated potassium carbonate solution and extracted with chloroform. This was worked up as above to give 12.9 g. of the same material for a combined yield of 37.8 g. (74%).

4-(1-methyl-1,2,3,6-tetrahydropyridine)ethanol (Intermediate for Example 10)

To a solution of 120 g. (3.0 mole) of sodium borohydride in one liter of absolute ethanol, 265 g. (1.0 mole) of 4-pyridineethanol methiodide in 1.2 liter of ethanol was added dropwise while maintaining a temperature of between 15°–25° C. The reaction product was evaporated to near dryness in vacuo, the residue treated with 500 ml. of water and extracted several times with chloroform. The chloroform solution was dried over sodium carbonate, filtered, and the residue distilled to give 68.8 g. b.p. 61°–65° C. (0.1 mm). A second crop was obtained upon further treatment of the aqueous residue with chloroform and worked up in the same manner.

3-(1,4-Dimethyl-1,2,5,6-tetrahydropyridine)methanol (Intermediate for Example 21)

To a suspension of 3.2 g. (0.084 mole) of lithium aluminum hydride in 160 ml. of ether, a solution of 4.3 g. (0.032 mole) of aluminum chloride in 60 ml. of ether was added. The free base obtained from 18 g. (0.08 mole) of ethyl 1,4-dimethyl-1,2,5,6-tetrahydronicotinate hydrochloride was dissolved in 60 ml. of ether and then was added slowly. The mixture was left overnight at room temperature and finally was refluxed for 3 hours. After the addition of 50 ml. of water, the mixture was extracted with ether and several times with chloroform, and again with chloroform after addition of 50 ml. of 50% sodium hydroxide solution. The combined organic extracts were dried over sodium carbonate and distilled. Two fractions were obtained:
A: 78°–82° C. (0.1 mm) 2.0 g.
B: 82°–94° C. (0.1 mm) 4.6 g.

Fraction B was found to be the desired compound. Fraction A was essentially the same as B but contained a small amount of impurity. The combined yield was 58%.

The 1,4-dimethyl-1,2,5,6-tetrahydronicotinate was obtained by the sodium borohydride reduction of ethyl 4-methyl-3-pyridinecarboxylate methiodide and was isolated as the hydrochloride salt.

PREPARATION OF DISUBSTITUTED GLYCOLIC ESTERS USING 1-METHYL-3-PYRROLINEMETHANOL AS THE AZACYCLIC ALCOHOL

EXAMPLE 25

3-(1-Methyl-3-pyrroline)methyl α-Isopropyl-α-phenylglycolate

To a solution of 1.13 g. (0.01 mole) of 3-(1-methyl-3-pyrroline)methanol and 2.0 g. (0.01 mole) of methyl α-isopropyl-α-phenylglycolate in 50 ml. of dry benzene, was added a small piece of sodium and the mixture heated under reflux while removing the benzene-methanol azeotrope. Upon completion of the reaction, the mixture was extracted with dilute hydrochloric acid. The acid layer was separated and made basic with a saturated potassium carbonate solution and extracted with chloroform. The residue obtained from the dried chloroform solution was distilled, and the fraction boiling at 156°–160° C./0.05 mm. collected as pure product.

Using the procedure of Example 25, the following disubstituted glycolic acids esterified with 3-(1-methyl-3-pyrroline)methanol were prepared.

TABLE II

| Example | R$_1$ | R$_2$ | B.P. °C. (mm) M.P. °C. | Mouse Screen MED$_{50}$ | LD$_{50}$ |
|---|---|---|---|---|---|
| 26 | C$_6$H$_5$ | △ | 133–4 | 0.02 | 56 |
| 27 | C$_6$H$_5$ | ☐ | 116–7 | 0.02 | 56 |
| 28 | C$_6$H$_5$ | ⬠ | 111–3 | 0.006 | 56 |
| 29 | ⬠ | —C≡C—CH$_3$ | 101–102.5 | 0.06 | 89 |
| 30 | C$_6$H$_5$ |  | 93–4 | 0.02 | 45 |

3-(1-methyl-3-pyrroline)methanol (Intermediate for Example 25)

A solution of 4.95 g. (0.037 moles) of aluminum chloride in 40 ml. of ether was added cautiously with stirring to a slurry of 3.79 g. (0.1 mole) of lithium aluminum hydride in 216 ml. of ether. After one hour, 15.5 g. (0.1 mole) of ethyl 1-methyl-3-pyrrolidine carboxylate in 80 ml. of ether was added dropwise while keeping the temperature between 5°–10° C. After three hours stirring at room temperature, 23.2 ml. of water was added cautiously at 20° C., the slurry filtered, and the cake washed with ether. The cake was then treated with 61.8 ml. of 50% sodium hydroxide solution, the resultant mixture filtered, and the filtrate extracted with chloroform. The residues from the ether and chloroform extracts were combined and distilled yielding 7.1 g. (62.8%) of product, b.p. 58°–64° C. (0.1 mm). The NMR spectrum confirmed the structure.

The ethyl 1-methyl-3-pyrrolidinecarboxylate was prepared by the reaction of thionyl chloride with ethyl 4-hydroxy-1-methyl-3-pyrrolidinecarboxylate followed by basifying with potassium carbonate.

The ethyl 4-hydroxy-1-methyl-3-pyrrolidinecarboxylate was obtained by reduction of the corresponding 4-pyrrolidone.

PREPARATION OF DISUBSTITUTED GLYCOLIC ESTERS USING 2-TROPIDINEMETHANOL AS THE AZACYCLIC ALCOHOL

Example 31

2-Tropidinemethyl α-Cyclopropyl-α-phenylglycolate

To a solution of 1.35 g. (0.01 mole) of 2-tropidinemethanol, 2.06 g. (0.01 mole) of methyl α-cyclopropyl-α-phenylglycolate in 70 ml. of dry benzene, was added a small piece of sodium and the mixture heated under reflux with the removal of the benzene-methanol azeotrope. Upon completion of the reaction, the mixture was extracted with dilute hydrochloric acid. The acid layer was separated and made basic with a saturated potassium carbonate solution and extracted with chloroform. The residue obtained from the dried chloroform solution was distilled. The material boiling at 180°–185° C./0.04 mm. was collected as pure material.

Using the procedure of Example 31, the following disubstituted glycolic acids esterified with 2-tropidinemethanol were prepared.

TABLE III

| Example | R$_1$ | M.P. °C. (mm.) B.P. °C. | Mouse Screen MED$_{50}$ | LD$_{50}$ |
|---|---|---|---|---|
| 32 | ☐ | 165–75(0.04) | 0.001 | 32 |
| 33 | ⬠ | 170–80(0.04) | 0.006 | 45 |
| 34 | —CH(CH$_3$)$_2$ | 165(0.03) | 0.006 | 45 |

2-Tropidinemethanol (Intermediate for Example 31)

To a slurry of 4.18 g. (0.11 mole) of lithium aluminum hydride in 600 ml. of ether (which had been stirred for one hour), a solution of 5.58 g. (0.042 mole) of aluminum chloride in 40 ml. of ether was added dropwise at room temperature, after which the mixture was cooled to 5°–10° C. After the dropwise addition of 18 g. (0.1 mole) of methyl 2-tropidinecarboxylate in 80 ml. of ether, the mixture was brought to room temperature, stirred for four hours, and let stand overnight. Water (65 ml.) was cautiously added, after which the mixture was extracted with ether and with chloroform. The aqueous residue was treated with 100 ml. of 50% sodium hydroxide and extracted several times with chloroform. The combined ether-chloroform extracts upon distillation gave two main fractions:

F$_1$: 2.0 g. b.p. 64°–79° C. (0.1 mm.)
F$_2$: 6.9 g. (45%) b.p. 79°–85° C. (0.1 mm.)

Fraction F$_2$ was shown by NMR to be mainly the desired product with some unidentified impurities amounting to 8.4% (VPC).

Anal. Calcd. for C$_9$H$_{15}$NO: C, 70.55; H, 9.87. Found: C, 70.28; H, 10.16.

PREPARATION OF DISUBSTITUTED GLYCOLIC ESTERS USING α-(1-AZABICYCLO[2.2.2.]OCT-2-ENE)ALKANOL AS THE AZACYCLIC ALCOHOL

EXAMPLE 35

3-(1-Azabicyclo[2.2.2.]oct-2-ene)methyl α-Isopropyl-α-phenylglycolate Hydrochloride A mixture of 1.39 g. (0.01 mole) of 3-(1-azabicyclo[2.2.2.]oct-2-ene)methanol, 2.1 g. of methyl α-isopropyl-α-phenylglycolate and 50 ml. of benzene, to which a small piece of sodium had been added, was heated under reflux with removal of the methanol-benzene azeotrope through a packed Vigreaux fractionating column. The mixture was cooled and extracted with dilute hydrochloric acid. The acid solution was made basic with a saturated potassium carbonate solution and extracted with chloroform. Some unreacted azacyclic alcohol was removed by sublimation. The residue from the sublimation was dissolved in ether and a small amount of insoluble material filtered off. The product was isolated as a crystalline hydrochloride by adding anhydrous hydrogen chloride to an ethereal solution of the basic ester. The hydrochloride salt was recrystallized from ethanol-ethyl acetate.

Using the procedure of Example 35, the following disubstituted glycolic acids esterified with 3-(1-azabicyclo[2.2.2.]oct-2-ene)methanol were prepared.

TABLE IV $$R-\underset{R_2}{\underset{|}{\overset{OH}{\overset{|}{C}}}}-COO-CH_2-\text{[azabicyclic]}$$

| Example | R$_1$ | R$_2$ | M.P., °C. B.P., °C. (mm.) | Mouse Screen MED$_{50}$ | LD$_{50}$ |
|---|---|---|---|---|---|
| 36 | C$_6$H$_5$ | C$_6$H$_5$ | 146–7 | 0.06 | 56 |
| 37 | C$_6$H$_5$ | △ | 182–60¹ | 0.02 | 32 |
| 38 | C$_6$H$_5$ | ▢ | 171–30¹ | 0.02 | 36 |

TABLE IV-continued

| Example | R$_1$ | R$_2$ | M.P., °C. B.P., °C. (mm.) | Mouse Screen MED$_{50}$ | LD$_{50}$ |
|---|---|---|---|---|---|
| 39 | C$_6$H$_5$ | cyclopentyl | 160–800¹ | 0.02 | 36 |
| 40 | C$_6$H$_5$ | cyclopentenyl | 108.5–109 | 0.02 | 36 |
| 41 | C$_6$H$_5$ | CH$_3$—C(=CH$_2$)— | 91.5–94 | 0.006 | 28 |
| 42 | cyclopentyl | CH$_3$—C≡C— | 90–91.5 | 0.06 | 56 |
| 43 | cyclopentyl | CH$_3$—C(=CH$_2$)— | 153–161 (.005) | 0.006 | 18 |

3-(1-Azabicyclo[2.2.2.]oct-2-ene)methanol (Intermediate for Example 35)

To 5.83 g. (0.153 mole) of lithium aluminum hydride which had been stirred with 200 ml. of ether for 1.5 hours, 6.85 g. (0.051 mole) of aluminum chloride was added with ice cooling. The mixture then was stirred at room temperature for 45 minutes. To this mixture was introduced 27.5 g. of 3-methoxycarbonyl-1-azabicyclo[2.2.2.]oct-2-ene in 100 ml. of ether while keeping the temperature at 15°–20° C. After stirring at room temperature for two hours, 40 ml. of water was added, the ether solution dried over sodium carbonate, and evaporated; the residue weighed 7.5 g. The ether insoluble material was made basic with 50% potassium hydroxide solution and was extracted first with ether and then with chloroform. The dry, combined ether-chloroform solutions yielded 20.1 g. of residue, which, upon distillation, gave two fractions:

F$_1$: b.p. 54°–70° C. (0.2 mm.) 5.0 g.
F$_2$: b.p. 70°–82° C. (0.2 mm.) 3.6 g.

The above partly crystallized fractions were combined and dissolved in a benzene-hexane mixture from which 2.5 g. of material, m.p. 80°–2° C. was obtained. Its NMR spectrum and chemical analysis substantiated the structure aforesaid.

EXAMPLE 44

2-(1-Azabicyclo[2.2.2.]oct-2-ene)methyl α-isopropyl-α-phenylglycolate Hydrochloride A small amount of sodium was added to a solution of 1.39 g. (0.01 mole) of 2-(1-azabicyclo[2.2.2.]oct-2-ene)-methanol and 2.08 g. (0.01 mole) of methyl α-isopropyl-α-phenylglycolate in benzene. Methanol, which was formed upon heating the solution under reflux, was removed as the methanol-benzene azeotrope. When no more methanol was distilled off, the benzene was removed in vacuo. The residue was treated with 200 ml. of boiling n-heptane and filtered. Upon cooling, some water soluble material deposited, which was filtered off and discarded. The clear n-heptane solution then was brought to dryness, the oily residue dissolved in ether, and a stream of hydrogen chloride passed through the solution. The precipitate which formed, was washed with ether and dissolved in ethyl acetate. The insoluble material was filtered off and discarded. From the ethyl acetate solution there was obtained 0.4 g. (11%) of crystalline material (A) m.p. 229°-30° C. A second crop (B) of 0.15 g. (4.1%), m.p. 170°-7° C. was obtained. Based on the NMR spectrum (A) was indicated to be the structure 2-(1-azabicyclo[2.2.2.]oct-2-ene)methyl α-isopropyl-α-phenylglycolate hydrochloride, and (B) was the structure 2-quinuclidinemethylene α-isopropyl-α-phenylglycolate hydrochloride; both samples contained some impurities.

The requisite 2-(1-azabicyclo[2.2.2.]oct-2-ene)methanol was obtained as follows:

To a slurry of 10 g. (0.26 mole) of lithium aluminum hydride in 500 ml. of ether (which had been stirred for one hour), a solution of 13.3 g. (0.1 mole) of aluminum chloride in 100 ml. of ether was added dropwise at room temperature over a period of 30 min. Stirring was continued for one hour and to the mixture, cooled to 5°-10° C., 47 g. (0.26 mole) of 2-ethoxycarbonyl-1-azabicyclo[2.2.2.]oct-2-ene in 200 ml. of ether was added dropwise. The mixture was stirred at room temperature for 4 hours and then left for 60 hours at room temperature. Water (65 ml.) was added and the cake which formed was washed with ether and several times with chloroform. The residues from the dried ether-chloroform solutions, upon treatment with petroleum ether and ether gave a crystalline material which after purification by sublimation weighed 11.6 g., m.p. 68°-73° C. The original aqueous residue was treated with 180 ml. of 50% sodium hydroxide solution and extracted with chloroform. This solution was dried over sodium carbonate, filtered and the solvent removed. Upon treating the residue in the same manner, 2.7 g. of the same material was obtained for a combined yield of 14.3 g. (40%). After sublimation the purified compound melted at 73°-6° C.

Examples 45 and 46 are obtained by the transesterification procedures previously described.

The $\Delta^3$-quinuclidineethanol used in Examples 45 and 46 was prepared as follows:

To a slurry of 10 g. (0.26 mole) of lithium aluminum hydride in 500 ml. of ether (which had been stirred for one hour), a solution of 13.3 g. (0.1 mole) of aluminum chloride in 100 ml. of ether was added dropwise at room temperature and the resultant mixture stirred for an additional hour. To this mixture, cooled to 5°-10° C., 50.7 g. (0.26 mole) of ethyl $\Delta^3$-quinuclidineacetate in 200 ml. of ether was added dropwise. Stirring was continued at room temperature for four hours, after which the mixture was allowed to stand overnight at room temperature. After the addition of 70 ml. of water at 20° C. and stirring for 20 minutes, the ether was filtered and the solid material was washed several times with ether and then with chloroform. The residues from the ether and chloroform extraction were combined and distilled. Two fractions were collected:

$F_1$: b.p. 86°-100° C. (0.4 mm.) 11.8 g.
$F_2$: b.p. 102°-4° C. (0.4 mm.) 4.8 g.

Upon treating $F_2$ with petroleum ether, it partly crystallized to give 3.4 g. of material ($F_2R$) m.p. 35°-41° C. (cloudy melt). $F_1$ was shown by NMR to be mainly starting material containing about 20% $F_2$.

Upon treating the residue from the ether and chloroform extractions with 175 ml. of 50% sodium hydroxide solution and extracting it with chloroform, additional material was obtained by distilling the chloroform residue.

$F_3$: 100°-4° C. (0.4) 4.0 g.

The NMR spectrum of $F_3$ showed it to be essentially the same as $F_2$ but containing a significant amount of an unidentified component. The NMR spectrum of $F_1R$ was consistent with the desired compound.

Toxicity and Symptomatology Test (TST)—Mouse

Each compound is administered by the lateral tail vein to Swiss albino male mice (weight range 18 to 25 grams). Mice are treated with doses logarithmically spaced beginning with 100.0 mg/kg and decreasing successively to a no-effect level. Two animals are used at each dosage level except in the determination of the minimal effective dose ($MED_{50}$) of interesting compounds. In the latter case, four mice for each dosage level are tested.

Individual observation of animals for all signs of activity, including reflex responses, are made at three, 15 and 30 minutes; at one, two, three, and four hours; and at 24-hour intervals thereafter until recovery. Only those mice are housed individually which seem to be in such poor condition that they might be expected to die overnight if grouped with those that have nearly or fully recovered. If deaths do occur overnight among grouped mice, then the doses at which death occurred are repeated with mice housed in separate cages. The results from this repeat test are used in estimating lethality.

In addition to the pharmacotoxic characterization at each dosage level, the animals are observed for coordination ability in climbing a vertical screen of ¼" mesh and a horizontal wire, in crossing ¼" Plexiglas horizontal strip, in climbing ¼" Plexiglas inclined strip, and in climbing down ½" metal vertical rod. The mice are stimulated to traverse these strips by the use of air currents which produce a sound stimulus. Thus, the two parameters measured are coordination and an escape

TABLE V

Preparation of Disubstituted Glycolic Esters Derived From A $\Delta^3$-Quinuclidinealkanol

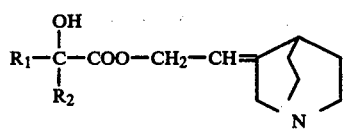

| Example | $R_1$ | $R_2$ | M.P. °C. | Mouse Screen $MED_{50}$ | $LD_{50}$ |
|---|---|---|---|---|---|
| 45 | $C_6H_5$ | (cyclopentyl) | 168 | 0.06 | 45 |
| 46 | $C_6H_5$ | $(CH_3)_2CH-$ | 93-4 | 0.02 | 45 | response from the air blast (an adverse stimulus). In addition, each animal is tested for altered sensitivity to sound as produced by several blasts of the Galton whistle. Each animal also is tested for locomotor deficit under forced locomotion on the rotating rod at 15 rpm. At each dosage level the animals are tested simultaneously at 15, 30, 60, and 120 minutes postinjection. The proportion of animals falling from the rod within one-minute tests at each dosage level are recorded.

Pupillary size in rabbits was estimated by comparison with a pupilometer during exposure to a constant, bright source of illumination initially and at selected intervals following intravenous treatment with 0.01 mg./kg. of compound. Five animals were used for each compound. Pupillary size was estimated periodically up to four-six hours and again 22–23 hours after dosing.

In the Tables, $MED_{50}$ is that dosage in mg/kg. of body weight in which ½ of the test animals exhibit definite effects of the candidate material. $LD_{50}$ is that dosage which produces 50% mortality in the test animals.

TABLE VI

Mydriatic Effect in Rabbits of Selected Glycolates $$C_6H_5-\underset{\underset{R}{|}}{\overset{\overset{OH}{|}}{C}}-COO-CH_2-R_2$$

| $R_1$ | $R_2$ | Mean Onset Time Minutes | Mean Time of Peak Effect Minutes | Mean Duration Minutes |
|---|---|---|---|---|
| —CH(CH₃)₂ | (1-methyl-tetrahydropyridinyl-methyl) | 20 | 66 | >360 |
| —CH(CH₃)₂ | (azabicyclic alkenyl) | 8 | 40 | 180 |
| (cyclopentenyl) | (1-methyl-tetrahydropyridinyl-methyl) | 11 | 18 | >60 |
| (cyclopentyl) | (azabicyclic alkenyl) | 6 | 121 | >360 |
| —CH(CH₃)₂ | (N-methyl bicyclic alkenyl) | 5 | 17 | 180 |

In Table VI measurement of the mydriatic effect in rabbits following treatment with glycolates is used as a basis for determining onset and duration of effect of this chemical class of compounds in vivo. The mydriatic effect is usually considered a manifestation of the peripheral cholinolytic activity of this class of compounds.

What is claimed is:
1. The compound 4-(1-methyl-1,2,3,6-tetrahydropyridine)methyl α-isopropyl-α-phenylglycolate.
2. The compound 4-(1-methyl-1,2,3,6-tetrahydropyridine)-methyl α-(1-cyclopentenyl)-α-phenylglycolate.

* * * * *